United States Patent
Roe (10) Patent No.: US 8,083,688 B2
(45) Date of Patent: Dec. 27, 2011

(54) SAMPLING DEVICES AND METHODS UTILIZING BIASED CAPILLARY ACTION

(75) Inventor: Steven N. Roe, San Mateo, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/706,015

(22) Filed: Feb. 16, 2010

(65) Prior Publication Data

US 2010/0145228 A1 Jun. 10, 2010

Related U.S. Application Data

(63) Continuation of application No. 10/732,615, filed on Dec. 10, 2003, now abandoned.

(60) Provisional application No. 60/436,331, filed on Dec. 24, 2002.

(51) Int. Cl.
*A61B 5/00* (2006.01)
*B65D 81/00* (2006.01)

(52) U.S. Cl. ........................ 600/583; 600/584

(58) Field of Classification Search .......... 600/583–584, 600/573, 576; 606/181–183
See application file for complete search history.

(56) References Cited

U.S. PATENT DOCUMENTS

| | | | |
|---|---|---|---|
| 3,623,475 A | 11/1971 | Sanz | |
| 4,360,016 A | 11/1982 | Sarrine | |
| 4,416,279 A | 11/1983 | Lindner et al. | |
| 4,503,856 A | 3/1985 | Cornell et al. | |
| 4,517,978 A | 5/1985 | Levin et al. | |
| 4,637,403 A | 1/1987 | Garcia et al. | |
| 4,653,513 A | 3/1987 | Dombrowski | |
| 4,850,973 A | 7/1989 | Jordan et al. | |
| 4,858,607 A | 8/1989 | Jordan et al. | |
| 4,869,249 A | 9/1989 | Crossman et al. | |
| 4,920,977 A | 5/1990 | Haynes | |
| 4,924,879 A | 5/1990 | O'Brien | |
| 5,139,489 A | 8/1992 | Hollister | |
| 5,230,864 A * | 7/1993 | Columbus | 422/520 |

(Continued)

FOREIGN PATENT DOCUMENTS

EP 0 166 574 1/1986

(Continued)

OTHER PUBLICATIONS

U.S. Appl. No. 10/165,101, filed Jun. 7, 2002 to Donnay et al.

*Primary Examiner* — Max Hindenburg
*Assistant Examiner* — Huong Nguyen
(74) *Attorney, Agent, or Firm* — Woodard, Emhardt, Moriarty, McNett & Henry LLP (57) ABSTRACT

A device is constructed so as to define a capillary channel that draws a body fluid form a proximal portion of the capillary channel toward a distal portion. A counterbore defining a "ledge" not substantially normal to the center line of channel causes the meniscus of body fluid to be "biased" into a non-radially-symmetric shape. In one example, the bias draws the body fluid toward a testing element that is set into a groove in the main body of the device. In another example, hydrophilic and/or hydrophobic regions are created on or in device to produce the biasing effect. In certain configurations, device requires less blood to be drawn into the capillary channel for a successful test than if the biasing effect were not created.

10 Claims, 6 Drawing Sheets

U.S. PATENT DOCUMENTS

| | | | |
|---|---|---|---|
| 5,298,224 | A | 3/1994 | Plum |
| 5,318,583 | A | 6/1994 | Rabenau et al. |
| 5,318,584 | A | 6/1994 | Lange et al. |
| 5,320,607 | A | 6/1994 | Ishibashi |
| 5,322,609 | A | 6/1994 | Graham |
| 5,368,047 | A | 11/1994 | Suzuki et al. |
| 5,402,798 | A | 4/1995 | Swierczek et al. |
| 5,879,311 | A | 3/1999 | Duchon et al. |
| 6,048,352 | A | 4/2000 | Douglas et al. |
| 6,051,392 | A | 4/2000 | Ikdeda et al. |
| 6,099,484 | A | 8/2000 | Douglas et al. |
| 6,146,361 | A | 11/2000 | DiBiasi et al. |
| 6,315,738 | B1 | 11/2001 | Nishikawa et al. |
| 6,332,871 | B1 | 12/2001 | Douglas et al. |
| 6,375,627 | B1 | 4/2002 | Mauze et al. |
| 6,468,287 | B1 | 10/2002 | Baugh |
| 6,485,439 | B1 | 11/2002 | Roe et al. |
| 6,571,651 | B1 | 6/2003 | Hodges |
| 6,612,111 | B1 | 9/2003 | Hodges et al. |
| 6,830,551 | B1 | 12/2004 | Uchigaki et al. |
| 6,866,675 | B2 | 3/2005 | Perez et al. |
| 2002/0049390 | A1 | 4/2002 | Allen et al. |
| 2002/0082522 | A1* | 6/2002 | Douglas et al. ............... 600/583 |
| 2002/0103499 | A1 | 8/2002 | Perez et al. |
| 2002/0177788 | A1 | 11/2002 | Hodges et al. |
| 2002/0188223 | A1 | 12/2002 | Perez et al. |
| 2003/0060730 | A1* | 3/2003 | Perez ........................... 600/576 |
| 2003/0191415 | A1 | 10/2003 | Moerman et al. |

FOREIGN PATENT DOCUMENTS

| | | |
|---|---|---|
| EP | 0 280 347 | 8/1988 |
| EP | 1 112 717 | 7/2001 |
| EP | 1 230 895 A1 | 8/2002 |
| JP | H07-155310 | 6/1995 |
| WO | WO 97/42885 A1 | 6/1998 |
| WO | WO 00/40150 | 7/2000 |
| WO | WO 01/72220 | 10/2001 |
| WO | WO 01/73395 | 10/2001 |
| WO | WO 02/100252 | 12/2002 |
| WO | WO 02/100276 | 12/2002 |
| WO | WO 02/100277 | 12/2002 |
| WO | WO 03/020134 | 3/2003 |

* cited by examiner

SAMPLING DEVICES AND METHODS UTILIZING BIASED CAPILLARY ACTION

REFERENCE TO RELATED APPLICATIONS

This application is a continuation of U.S. application Ser. No. 10/732,615, filed Dec. 10, 2003 now abandoned, which claims the benefit of U.S. Provisional Application No. 60/436,331, filed Dec. 24, 2002, which are hereby incorporated by reference in their entirety.

BACKGROUND

The present invention generally relates to the medical field, and more specifically, but not exclusively, relates to the sampling of bodily fluids.

The acquisition and testing of body fluids is useful for many purposes, and continues to be of importance for use in medical diagnosis and treatment, and in other diverse applications. In the medical field, it is desirable for lay operators to perform tests routinely, quickly and accurately outside of a laboratory setting, with rapid results and a read-out of the resulting test information. Testing can be performed on various body fluids, and for certain applications, it is particularly related to testing of blood and/or interstitial fluid. Such fluids can be tested for a variety of characteristics of the fluid or analytes contained in the fluid, in order to identify medical conditions, determine therapeutic responses, assess progress of treatments and the like.

A common medical test is the measurement of blood glucose levels. The glucose level can be determined directly by analysis of the blood, or indirectly by analysis of other fluids, such as interstitial fluid. Diabetics are generally instructed to measure their glucose levels several times a day, depending on the nature and severity of their diabetes. Based upon observed patterns in the measurement of glucose levels, the patient and physician can determine the appropriate level of insulin to be administered, also taking into account such issues as diet, exercise and other factors.

In testing for the presence of analytes such as glucose in a body fluid, test systems are commonly used which take advantage of oxidation/reduction reaction, which occurs using an oxidase/peroxidase detection chemistry. The testing reagent is exposed to a sample of the body fluid for a suitable period of time, and there is a color change if analyte (glucose) is present. Typically, the intensity of the change is proportional to the concentration of analyte in the sample. The color of the reagent is then compared to a known standard, which enables one to determine the amount of analyte present in the sample. This determination can be made, for example, by visual check or by an instrument, such as a spectrophotometer at a selected wave length, or a blood glucose meter. Electrochemical and other systems are also well known for testing body fluids for properties of constituents. Typically, a fingertip or some other body location of a patient is lanced with a lancet in order to obtain a body fluid sample.

Although fingertips generally provide an ample supply of blood, repeated lancing of fingertips can be quite painful due to the high concentration of nerve endings in the fingertips. Therefore, there has been a trend towards sampling fluids from alternate sites on the body, where the nerve concentrations are lower, such as the forearm. As should be appreciated, since alternate sites have lower nerve concentrations, the patient experiences less pain when lancing the alternate site. However, these alternate sites usually produce less fluid as compared to fingertips. Consequently, it has been a goal to reduce the amount of fluid needed for a successful test. To achieve this goal, it is desirable to ensure that as much fluid as possible is transported from the incision to the test area so as to minimize waste.

Thus, there remains a need for improvement in this field.

DETAILED DESCRIPTION OF PREFERRED EMBODIMENTS

Provided below is a written description of examples embodying the invention and examples of making and using the same. The scope of the invention is not limited to these examples, but rather is defined solely by the numbered claims that appear at the end of this document, and the invention includes alterations, modifications, and further applications that fall within the claims. The written description uses full, clear, concise, and exact terms to enable any person skilled in the art to which the invention pertains to make and use the invention. The best mode contemplated by the inventor of carrying out the invention is also set forth herein.

All the information set forth in the following patent applications is incorporated by reference, as if fully set forth herein: U.S. patent application Ser. No. 10/054,270, filed Jan. 22, 2002, entitled LANCET DEVICE HAVING CAPILLARY ACTION; and U.S. patent application Ser. No. 10/165, 101, filed Jun. 7, 2002, entitled SAMPLING DEVICES AND METHODS UTILIZING A HORIZONTAL CAPILLARY TEST STRIP.

Figure 1:
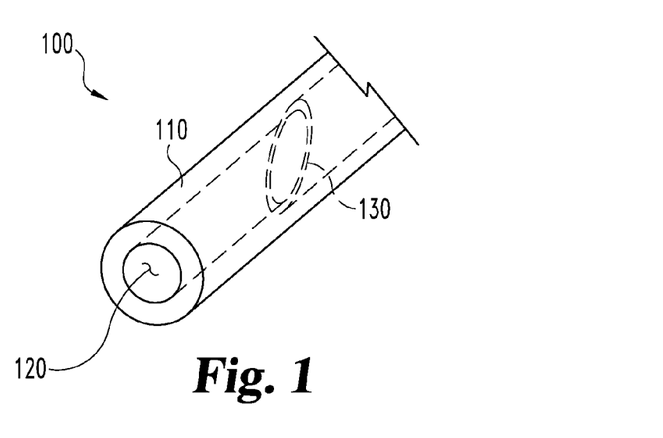
FIG. 1 is an isometric view of a portion of an example apparatus according to the present invention.

The present invention generally concerns a sampling device that is configured to bias the flow of body fluid in the device so as to reduce the amount of fluid needed for sampling. In one embodiment, the device has a capillary channel that is structured to bias a miniscus of the fluid in a radially asymmetric manner. Specifically, the capillary channel has an angled counter bore that biases the meniscus of the fluid in a radial asymmetric manner. In another embodiment, the capillary channel includes hydrophobic and hydrophillic portions that bias the flow of fluid. FIG. 1 illustrates one example of a device 100 for sampling body fluid (not shown), comprising a main body 110 defining a capillary channel 120. The capillary channel 120 is preferably dimensioned to draw a body fluid into the capillary channel 120 through capillary action, as described more fully in the above-incorporated patent applications. In this example the capillary channel 120 is further dimensioned to form an angled counterbore 130. Though the device 100 is shown in FIG. 1 as cylindrical with an annular cross-section, this is just one example geometry. Any geometry can be used for device 100, as long as device 100 provides a capillary channel 120 dimensioned to draw a body fluid into said capillary channel 120 through capillary action. For example, one or more portions of device 100 and/or capillary channel 120 could independently have square, rectangular, triangular, oval, U-shaped, amorphous, or any other shape cross-sections. Device 100 may comprise any material and may be made by any means, such as the materials and methods of manufacture set forth in the above-incorporated patent applications.

Figure 2A:
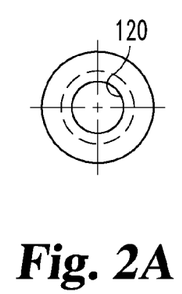
FIG. 2A is an end view of the apparatus of FIG. 1.
Figure 2B:
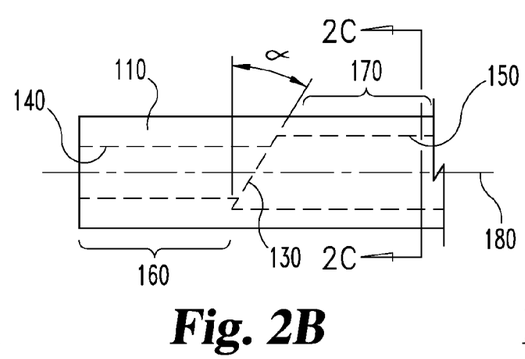
FIG. 2B is a side view of the apparatus of FIG. 1.
Figure 2C:
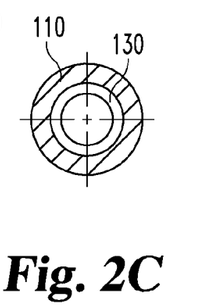
FIG. 2C is a cross-sectional view taken along line 2C-2C of FIG. 2B.

FIGS. 2A, 2B and 2C further illustrates the example of FIG. 1. The device, or apparatus, 100 comprises a body 110 defining a capillary channel 120 having a first region 140 and a second region 150 and a proximal portion 160 and a distal portion 170. In the example shown in FIGS. 1-5, the second region 150 of the capillary channel 120 defines a counterbore 130 ending in a surface non-normal to the longitudinal axis 180 of the capillary channel 120 by angle α.

Figure 3:
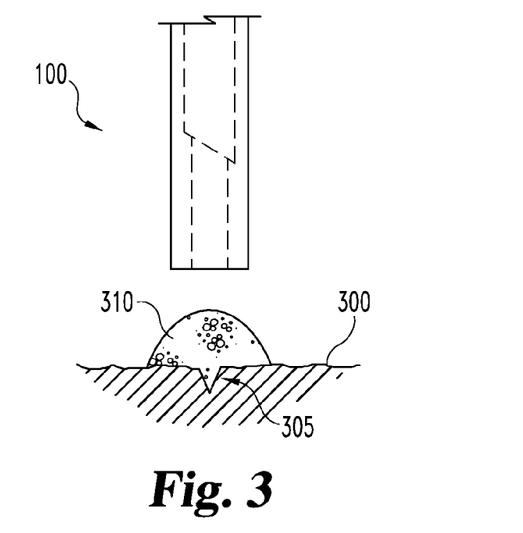
FIG. 3 is a side view of the apparatus of FIG. 1 disposed above body fluid on a tissue surface.
Figure 4:
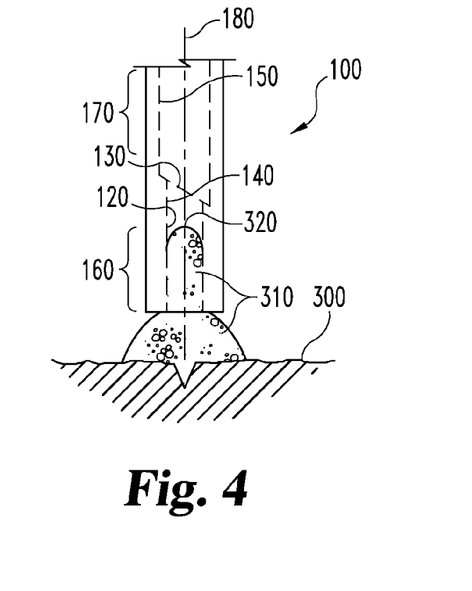
FIG. 4 is a side view illustrating the apparatus of FIG. 1 displaying the initial capillary action.
Figure 5:
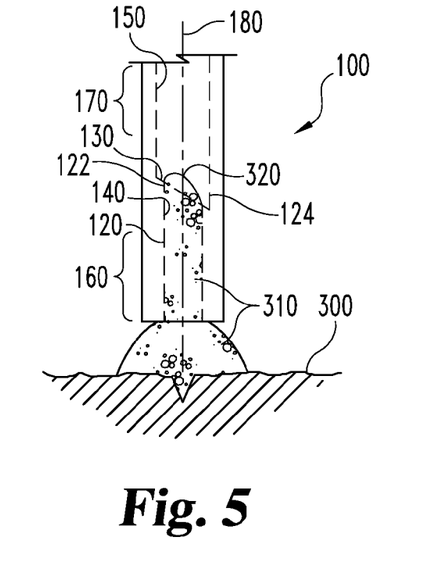
FIG. 5 is a side view illustrating the apparatus of FIG. 1 displaying biased capillary action.

FIG. 3 illustrates the device 100 positioned above a drop of body fluid 310 issuing from an incision 305 in body tissue 300. The body fluid 310 may be produced by puncturing the body tissue 300, or by any other means, including as described in the above-incorporated patent applications. FIG. 4 illustrates the device 100 lowered toward the body tissue 300 until the proximal portion 160 of the capillary channel 120 is in fluid communication with the body fluid 310. The body fluid 310 is then drawn into the capillary channel 120 by capillary action, as represented in FIGS. 4 and 5. As shown in FIGS. 4 and 5, the body fluid 310 flows in the capillary channel 120 from the proximal portion 160 toward the distal portion 170. However, when the body fluid 310 reaches the angled counterbore 130, the meniscus 320 of the body fluid 310 is biased radially asymmetrically about the centerline 180 toward one side of capillary channel 120, as shown in FIG. 5.

Capillary mechanics dictate that the step or offset created by the angled counterbore 130 causes the first region 140 to have an effectively stronger capillary attraction to body fluid 310 than the second region 150 when the body fluid 310 flows in the capillary channel 120 from the proximal portion 160 toward the distal portion 170. Though an angled counterbore 130 is shown as an example, any geometry including a step or other shape can be used that has the capillary biasing effect of biasing the forces of capillary action acting on body fluid 310 so that they are radially asymmetric about the centerline 180, such as by tending to favor one side of capillary channel 120.

This difference in capillary attraction pulls or biases the meniscus 320 radially asymmetrically about the centerline 180, toward the first region 140 and away from the second region 150, thus biasing the body fluid 310 toward a first side 122 of the capillary channel 120, and away from a second side 124 of the capillary channel 120. Subject to the materials and dimensions used in device 100 and their interaction with a particular body fluid 310, increasing the angle α tends to increasingly bias the body fluid 310 toward a first side 122 of the capillary channel 120, and away from a second side 124 of the capillary channel 120.

Figure 6:
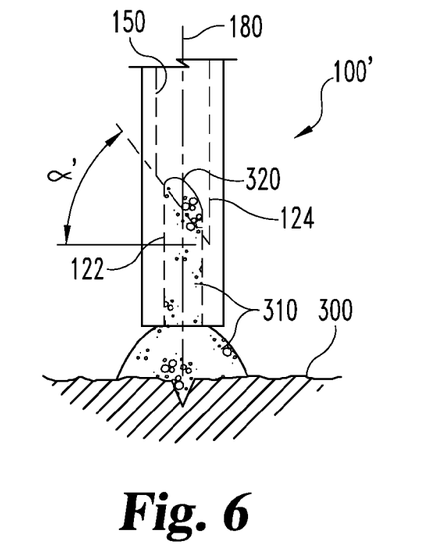
FIG. 6 is a side view of a portion of an alternative example apparatus according to the present invention displaying another form of biased capillary action.

FIG. 6 shows a device 100' that is similar to device 100, but has a counterbore 130' with an increased angle α'. As shown in FIG. 6, increasing the angle from α to α' tends to increase the bias of the meniscus 320 radially asymmetrically about the centerline 180, thus tending to increase the bias of the body fluid 310 toward a first side 122 of the capillary channel 120, and away from a second side 124 of the capillary channel 120.

Figure 7:
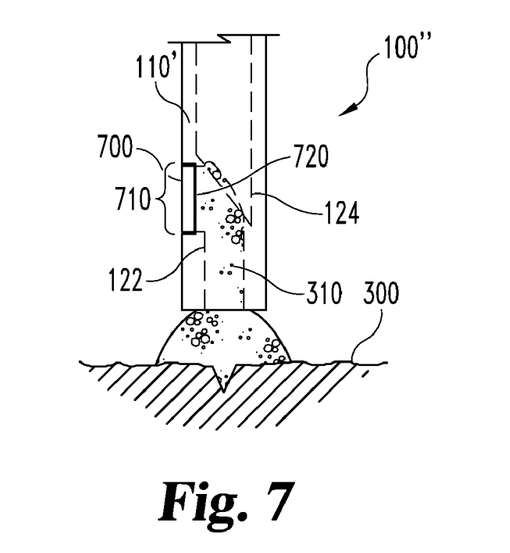
FIG. 7 is a side view of the apparatus of FIG. 6 illustrating a test strip disposed within a groove in the apparatus.

FIG. 7 shows the device 100' of FIG. 6 further including a testing element 700 disposed within a groove 710 in the main body 110' of the device 100". When body fluid 310 has moved up first side 122, as shown, the testing element 700 is in spatial communication with body fluid 310 through one or more passageways 720, so that the testing element 700 may be used to test various aspects of the body fluid 310, for instance as described in the above-incorporated patent applications. Testing element 700 may be any testing means that interfaces with body fluid 310, such as a test strip or other chemistry, for instance as described in the above-incorporated patent applications. In one embodiment, the testing element 700 includes a membrane.

Since the body fluid 310 tends to bias toward the first side 122 of the capillary channel 120, passageways 720 are shown formed in the first side 122 of the capillary channel 120. Passageways 720 are filled with body fluid 310, even though the adjacent portion of the capillary channel 120 is only partially filled with body fluid 310 due to the biasing effect described above.

Thus, the device 100" is capable of communicating body fluid 310 to testing element 700 using less body fluid 310 than would be required without the capillary biasing effect described herein.

Figure 8:
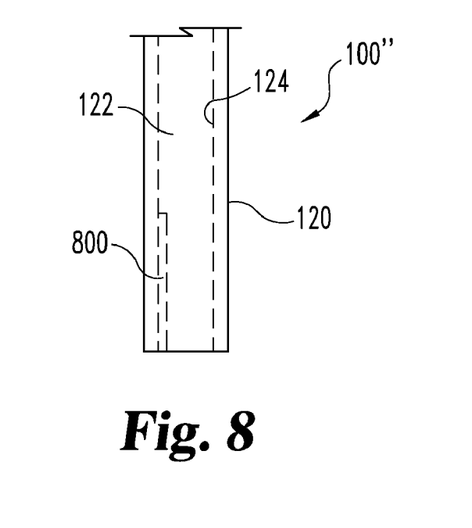
FIG. 8 is a side view of a portion of another alternative example apparatus according to the present invention.

FIG. 8 illustrates another example device 100‴ configured to create a capillary biasing effect without requiring an angled counterbore 130 or any geometry such as a step or other shape in the capillary channel 120. Instead, the first side 122 of the capillary channel 120 includes a hydrophilic region 800. The hydrophilic region 800 is hydrophilic relative to one or more adjacent regions of the capillary channel 120, such as the second side 124. The hydrophilic region 800 need only be relatively hydrophilic; for instance, the hydrophilic region 800 may be defined by providing hydrophobic surrounding regions. A relatively hydrophilic region 800 may be created by forming portions of the capillary channel 120 from hydrophilic or hydrophobic materials, or by treating portions to be relatively hydrophilic or hydrophobic, for instance in the manners described in the above-incorporated patent applications.

Figure 9:
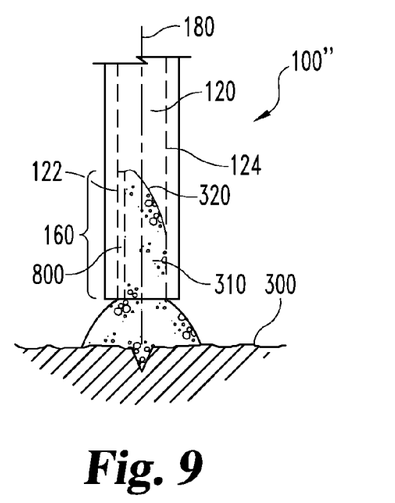
FIG. 9 is a side view of the apparatus of FIG. 8 displaying another form of biased capillary action.

FIG. 9 illustrates the device 100‴ of FIG. 8 positioned near body tissue 300 so that the proximal portion 160 of the capillary channel 120 is in fluid communication with a small drop of body fluid 310 issuing from an incision 305 in body tissue 300, the body fluid 310 being drawn into the capillary channel 120 by capillary action. When the body fluid 310 reaches the relatively hydrophilic region 800, the body fluid 310 is disproportionately attracted to the hydrophilic region 800. This difference in capillary attraction pulls or biases the meniscus 320 radially asymmetrically about the centerline 180, thus biasing the body fluid 310 toward the relatively hydrophilic region 800 of the first side 122 of the capillary channel 120, and away from the relatively hydrophobic second side 124 of the capillary channel 120.

Figure 10:
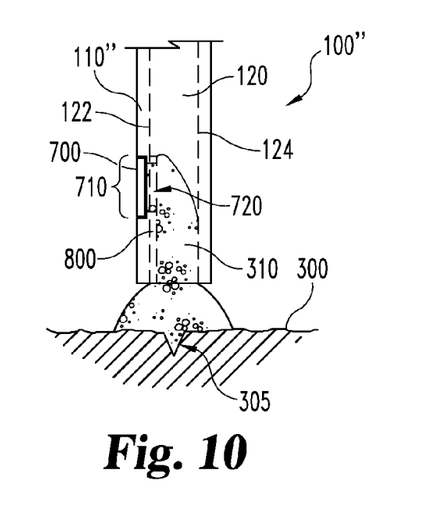
FIG. 10 is a side view of the apparatus of FIG. 8 illustrating a test strip disposed within a groove in the apparatus.

FIG. 10 shows the device 100‴ of FIG. 9 further including a testing element 700 disposed within a groove 710 in the main body 110‴ of the device 100‴. The testing element 700 is in spatial communication with body fluid 310 through one or more passageways 720, so that the testing element 700 may be used to test various aspects of the body fluid 310, as set forth above.

Since the body fluid 310 tends to bias toward the hydrophilic region 800 on the first side 122 of the capillary channel 120, passageways 720 are shown formed in the first side 122 of the capillary channel 120. Passageways 720 are filled with body fluid 310, even though the adjacent portion of the capillary channel 120 is only partially filled with body fluid 310 due to the biasing effect described above. Thus, the device 100" is capable of communicating body fluid 310 to testing element 700 using less body fluid 310 than would be required without the capillary biasing effect described herein.

Figure 11:
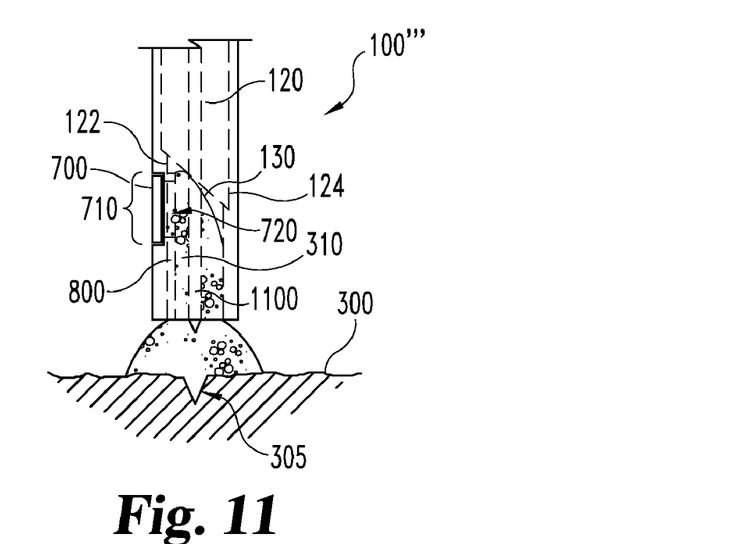
FIG. 11 is a side view of a portion of yet another alternative example apparatus according to the present invention.

FIG. 11 shows a device 100''' including by way of example both an angled counterbore 130 and a relatively hydrophilic region 800 in the capillary channel 120, and further including an integrated lancet 1100 for forming the incision 305. The integrated lancet 1100, or any other structure, may be used in conjunction with devices incorporating the capillary biasing effect described herein. For instance, devices including an integrated lancet 1100 can include any or all of the structure set forth in the above-incorporated patent applications. In this example, an angled counterbore 130 works in conjunction with a relatively hydrophilic region 800 to bias body fluid 310 toward testing element 700 using less body fluid 310 than would be required without the capillary biasing effect described herein.

Figure 12:
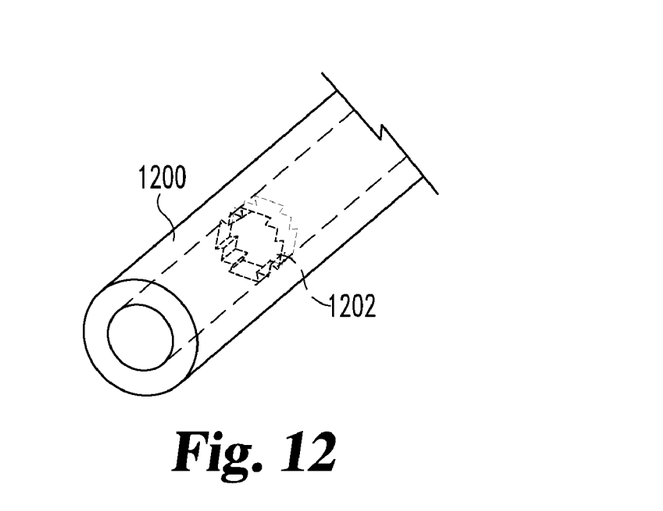
FIG. 12 is an isometric view of a portion of another example apparatus according to the present invention.

FIG. 12 illustrates a capillary tube 1200 according to another embodiment of the present invention. In the illustrated embodiment, the capillary tube 1200 has a stepped-end counterbore 1202 for biasing the fluid in a specified direction inside the capillary tube.

Various alternatives to the structures and details described herein are available, and could be implemented without undue experimentation by those skilled in the art. For example, a plurality of sites on a testing device might be used for testing the same or different characteristics of the body fluid. Those sites might be spaced around the circumference of the device at approximately the same distance from the proximal end, or they might be situated at different distances from the proximal end. They may be on the same side of the device, opposite sides of the device, or in some other relative configuration.

Further, various test methods may be implemented at the one or more test sites, including for example optical, magnetic, and chemical tests as would occur to one skilled in the art given the disclosure herein, which includes the matter incorporated by reference above.

Furthermore, a wide variety of techniques might be used to bias the body fluid toward the testing site(s). These techniques might include (but are not limited to) the angled-end counterbore and hydrophobic/hydrophilic wall techniques discussed above; chemically treating or coating one or more portions of the inner wall of the capillary tube with one or more different hydrophobic, hydrophilic, or other chemicals known in the art; the stepped-end counterbore 1202 as shown in FIG. 12; roughening the inner wall of the capillary tube in one region relative to another; and forming longitudinal grooves in certain portions of the inner wall (or more grooves in certain portions than in others).

While examples embodying the invention have been illustrated and described in detail in the drawings and foregoing description, which includes material incorporated by reference, these examples are illustrative and not restrictive in character, it being understood that only certain examples have been shown and described and that all changes and modifications that come within the spirit of the invention are to be protected.

What is claimed is:

1. A method, comprising:
   providing a body fluid sampling device that includes
      a capillary channel with a capillary channel wall with a first side and a second side that opposes the first side, wherein the capillary channel has a proximal end portion with a capillary channel opening and a distal end portion that extends opposite the proximal end portion, wherein the capillary channel extends from the proximal end portion to the distal end portion along a longitudinal axis,
      a testing element disposed along the first side of the channel wall between the proximal end portion and the distal end portion, wherein the testing element and the channel wall are distinct from one another,
      a lancet disposed within the capillary channel and defining a capillary space between the lancet and the channel wall of the body, wherein the channel wall of the capillary channel surrounds the lancet,
      wherein the first side of the capillary channel wall has a relatively hydrophilic region that extends from the capillary channel opening to the testing element where the hydrophilic region ends, wherein the hydrophilic region has a higher hydrophilic affinity relative to the second side of the capillary channel wall, and
      wherein the capillary channel defines a counterbore ending in a surface that is non-normal to the longitudinal axis of the capillary channel;
   lancing an incision in tissue with the lancet by extending the lancet from the capillary channel opening;
   drawing body fluid from the incision via capillary action into the capillary space, wherein the body fluid forms a meniscus in the capillary space;
   biasing the meniscus in an asymmetric manner with the hydrophilic region and the counterbore towards the testing element, wherein the counterbore works in conjunction with the hydrophilic region to bias the body fluid towards the testing element to use less of the body fluid than would be required without biasing the body fluid in the asymmetric manner;
   wherein the counterbore is angled in an asymmetric manner at the distal end portion of the capillary channel;
   wherein the capillary channel has a diameter;
   wherein the counterbore has a diameter larger than the diameter of the capillary channel;
   wherein the testing element is disposed between the counterbore and the hydrophilic region;
   wherein the hydrophilic region extends only from the capillary channel opening to the testing element, wherein the hydrophilic region ends at the testing element, wherein the hydrophilic region is absent along the capillary channel wall from the testing element towards the distal end portion; and
   wherein said biasing meniscus includes ceasing flow of the body fluid at the testing element with the counterbore.

2. The method of claim 1, further comprising:
   analyzing the body fluid with the testing element.

3. A device for sampling body fluid, comprising:
   a body defining a capillary channel with a channel wall having a first side and a second side opposing the first side, the capillary channel having a proximal end portion with a capillary channel opening where the body fluid is drawn into the capillary channel and a distal end portion that extends opposite the proximal end portion, wherein the capillary channel extends from the proximal end portion to the distal end portion along a longitudinal axis;

a testing element disposed along the first side of the channel wall between the proximal end portion and the distal end portion, the testing element and the channel wall being distinct from one another;

a lancet disposed within the capillary channel and defining a capillary space between the lancet and the channel wall of the body, wherein the channel wall of the capillary channel surrounds the lancet, the capillary channel being dimensioned to draw the body fluid into the capillary space through capillary action;

the first side of the capillary channel wall having a relatively hydrophilic region that extends from the capillary channel opening to the testing element where the hydrophilic region ends, wherein the hydrophilic region has a higher hydrophilic affinity relative to the second side of the capillary channel wall to bias a meniscus of the body fluid toward the testing element when the body fluid is drawn into the space;

wherein the capillary channel defines a counterbore ending in a surface that is non-normal to the longitudinal axis of the capillary channel, wherein the counterbore works in conjunction with the hydrophilic region to bias the body fluid towards the testing element to use less of the body fluid than would be required without biasing the body fluid in an asymmetric manner;

wherein the counterbore is angled in an asymmetric manner at the distal end portion of the capillary channel;

wherein the capillary channel has a diameter;

wherein the counterbore has a diameter larger than the diameter of the capillary channel; and wherein the testing element is disposed between the counterbore and the hydrophilic region, the counterbore being located at the distal end portion to inhibit the body fluid from flowing into the distal end portion.

4. The device of claim 3, wherein the proximal end portion and the distal end portion are shaped to draw the body fluid towards the test element.

5. The device of claim 4, wherein the proximal end portion and the distal end portion form a stepped-end counter bore.

6. The device of claim 4, wherein the proximal end portion and the distal end portion of the channel wall define an angled counterbore adapted to impart a radially asymmetric bias to the meniscus of the body fluid when the fluid is within the capillary channel.

7. The device of claim 6, wherein said bias tends to bias said fluid toward a testing element in spatial communication with said fluid.

8. The device of claim 7, wherein said testing element comprises a test strip.

9. The device of claim 8, wherein said test strip comprises a membrane.

10. The device of claim 8, wherein said test strip is mounted in a groove defined in said device.

* * * * *